United States Patent [19]

Ueno

[11] Patent Number: 5,175,008
[45] Date of Patent: Dec. 29, 1992

[54] DEVICE FOR SUPPLYING PLASTIC MATERIAL FOR DENTURE BASE AND FLASK WITH THE SAME

[75] Inventor: Masato Ueno, Hiroshima, Japan

[73] Assignee: Chugoku Shiken Kabushiki Kaisha, Hiroshima, Japan

[21] Appl. No.: 764,120

[22] Filed: Sep. 24, 1991

Related U.S. Application Data

[63] Continuation of Ser. No. 440,542, Nov. 22, 1989, abandoned.

[30] Foreign Application Priority Data

Nov. 24, 1988 [JP] Japan ................. 63-296798

[51] Int. Cl.⁵ .......................................... B29C 39/24
[52] U.S. Cl. ............................... 425/178; 249/54; 249/82; 249/111; 425/180; 425/555
[58] Field of Search ................ 249/54, 82, 111; 425/555, DIG. 11, 2, 556, 175, 178, 55, 177, 179, 180, 176; 264/2.2, 17, 18

[56] References Cited

U.S. PATENT DOCUMENTS

| | | | |
|---|---|---|---|
| 1,533,625 | 4/1925 | Williams | 264/17 |
| 1,875,660 | 9/1932 | Rodin | 425/178 |
| 1,926,508 | 9/1933 | Ballard | 425/179 |
| 2,036,179 | 3/1936 | MacBrair et al. | 425/175 |
| 2,072,349 | 3/1937 | Wayne | 425/555 |
| 2,118,764 | 5/1938 | McWane | 249/82 |
| 2,341,991 | 2/1944 | Jackson | 264/18 |
| 2,359,152 | 9/1944 | Pryor et al. | 264/17 |
| 2,554,960 | 5/1951 | Scharfe | 425/179 |
| 2,574,594 | 11/1951 | Scharfe | 425/175 |
| 2,576,224 | 11/1951 | Hordes | 249/54 |
| 2,592,376 | 4/1952 | Ballard | 249/54 |
| 2,981,976 | 5/1961 | Maier | 425/555 |
| 3,005,105 | 10/1961 | Lusk | 249/111 |
| 3,680,625 | 8/1972 | Hein et al. | 249/111 |
| 3,964,539 | 6/1976 | Hodler | 249/82 |
| 4,022,419 | 5/1977 | Haker | 425/175 |

FOREIGN PATENT DOCUMENTS

| | | | |
|---|---|---|---|
| 849476 | 2/1951 | Fed. Rep. of Germany . | |
| 838748 | 5/1952 | Fed. Rep. of Germany | 264/18 |
| 901581 | 1/1954 | Fed. Rep. of Germany | 264/18 |
| 911897 | 5/1954 | Fed. Rep. of Germany | 264/18 |
| 3322343 | 1/1985 | Fed. Rep. of Germany .. | |
| 1305138 | 11/1961 | France | 249/111 |
| 485124 | 10/1953 | Italy | 264/18 |
| 56-144123 | 11/1981 | Japan | 249/82 |

OTHER PUBLICATIONS

Plastics Engineering vol. 35, No. 6, Jun. 1979, pp. 41-44 Greenwich, GB; W. G. Halstead et al. "Processing--Vary the volume, control the shrinkage".
"SR-IVOCAP System" (by Ivoclar of Liechtenstein), QDT Journal, advertising pages. No date.

*Primary Examiner*—Jay H. Woo
*Assistant Examiner*—Robert B. Davis
*Attorney, Agent, or Firm*—Armstrong & Kubovcik

[57] ABSTRACT

A device for supplying plastic material into a flask under pressure and a flask with the device, which are used for preparation of a denture. The device includes a cylinder having the inside end communicated to a cavity in the flask, a piston slidably inserted in the cylinder, a spring urging the piston toward inside of the flask, a stopper restricting the outside stroke end of the piston, and a device for adjusting elastic force of the spring. The adjusting device preferably includes a spring receiver abutting against the outside end of the spring, a screw-mechanism for moving the spring receiver in the axial direction of the cylinder, and a handle member for operating the screw-mechanism.

7 Claims, 12 Drawing Sheets

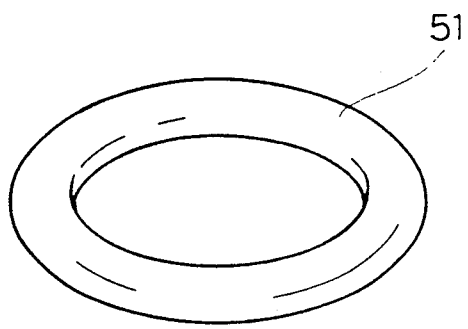
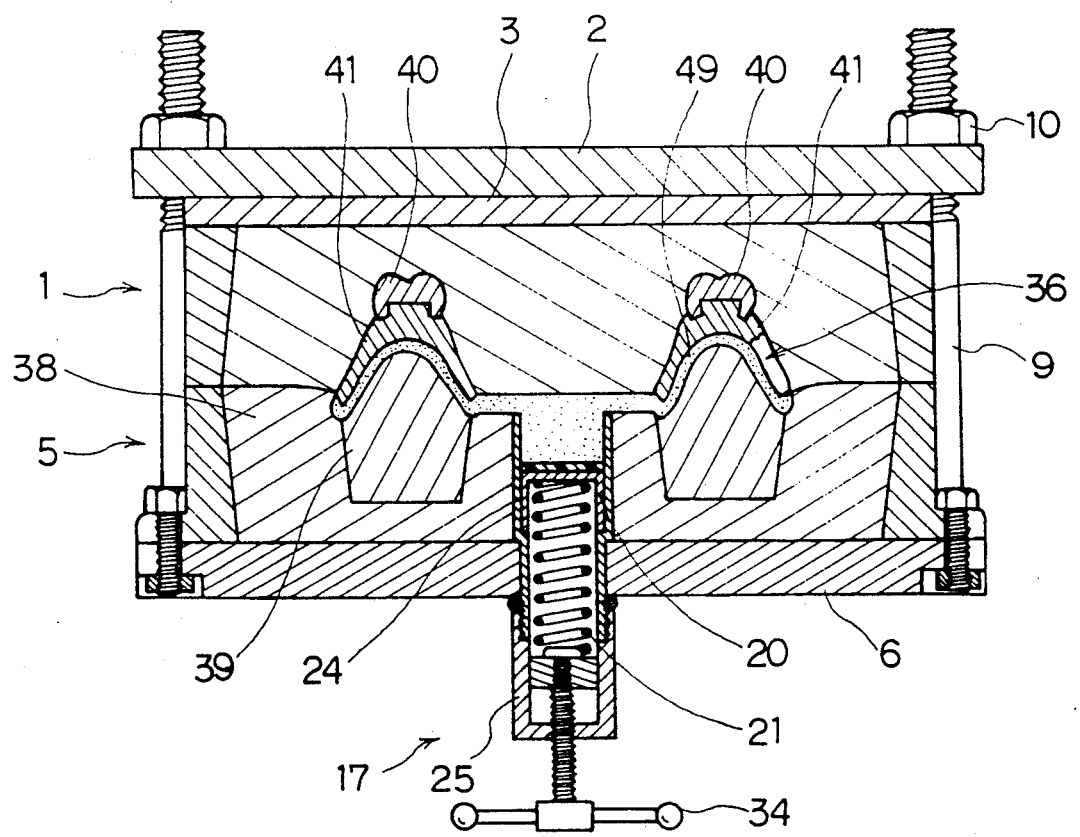

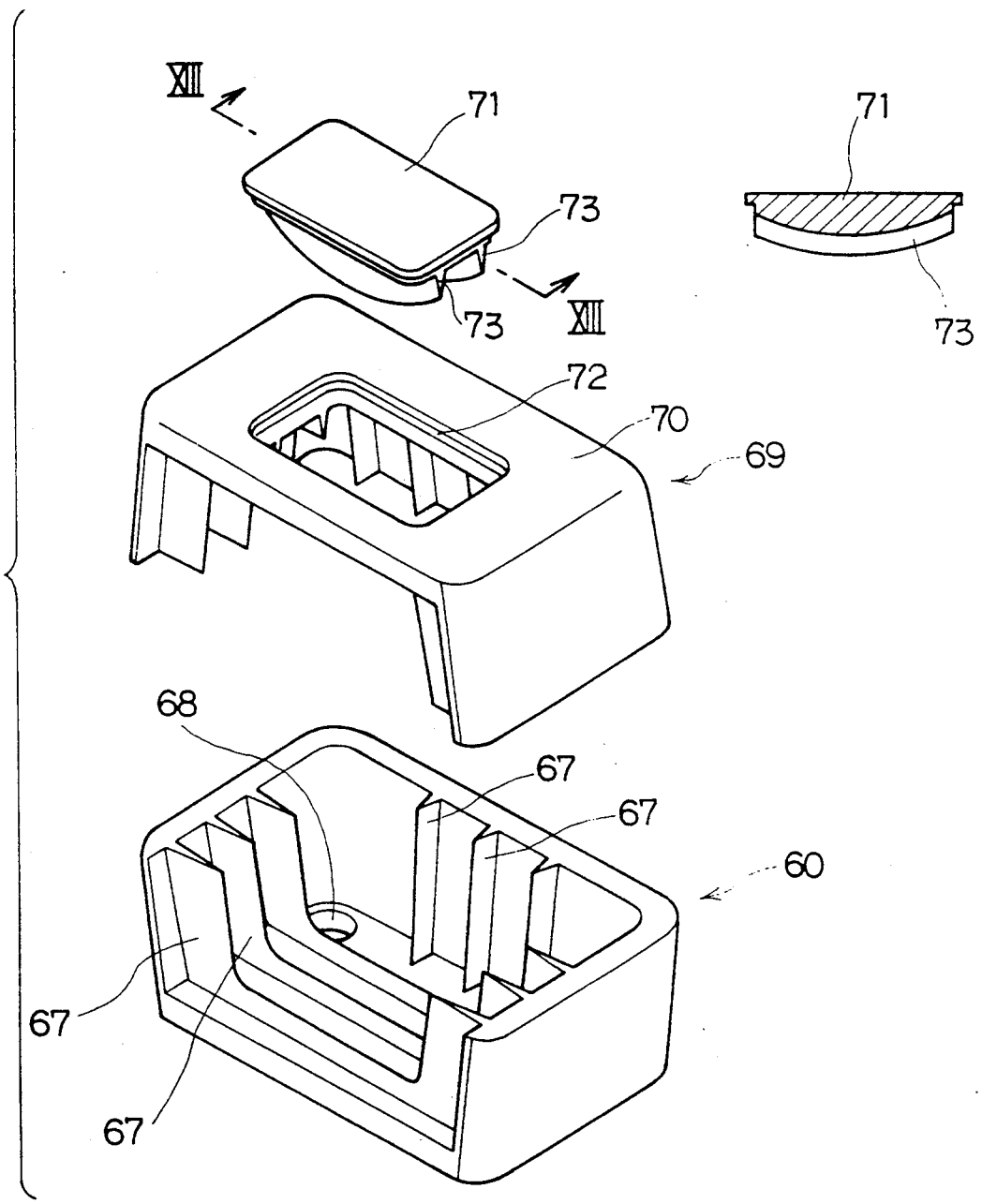

DEVICE FOR SUPPLYING PLASTIC MATERIAL FOR DENTURE BASE AND FLASK WITH THE SAME

This application is a continuation now abandoned of application Ser. No. 440,542 filed Nov. 22, 1989.

BACKGROUND OF THE INVENTION

The present invention relates to a device for supplying plastic material for denture base and a flask with the same.

There has been hitherto known a device for supplying plastic material for a denture base, e.g. polymethyl methacrylate (PMMA) as disclosed, for example, in Japanese Unexamined Utility Model Publication No. 145519/1986.

Further, there has been known an art to apply a plastic material, e.g. thermoplastic elastomer, on a backside (to be in contact with a mucous membrane) of a denture in order to form a lining, for example, as disclosed in Japanese Unexamined Patent Publication No. 342/1987.

By blending powder of PMMA with liquified methyl methacrylate (MMA) monomer, kneading the blend to obtain a plastic (dough) material, compressing the material in between a set of plaster models, and heating the material in hot water or vapour of about 100° to 130° C. for a period, the MMA material is polymerized and set, and then a denture base is obtained.

During the initial stage of polymerization, the material expands due to boiling of the liquid MMA monomer, heat-expansion of PMMA, and the like. As polymerization and cooling progress, the material shrinks, and heat-deformation results.

The above-mentioned Japanese Unexamined Utility model Publication No. 145519/1986 disclosed a device having a piston and cylinder for supplying the shortage of PMMA when the material shrinks. However, that device has a drawback in that bubbles and cavities tend to be produced in the denture bases, because the PMMA material expands initially, then shrinks.

Further, the above-mentioned Japanese Unexamined Patent Publication No. 342/1987 discloses a device for forming a liner made of thermoplastic elastomer and for fixing the liner on the backside of a denture base when PMMA material is polymerized and set under heating at the same time. However, the thermoplastic elastomer also expands under heating, and shrinks when cooled. Thus, bubbles and cavities are generated in the resulting liner also.

The main object of the present invention is to provide a device for supplying plastic material for denture base or the like, which does not produce bubbles and cavities in the denture base or the like.

SUMMARY OF THE INVENTION

According to the first aspect of the present invention, there is provided a device for supplying plastic material into a flask, comprising a cylinder having an inside end opening into the cavity of a flask, a piston slidably inserted in the cylinder, a spring urging the piston toward the inside of the flask, a stopper restricting the outside stroke end of the piston, and a means for adjusting the elastic force of the spring.

The means for adjusting the elastic force of the spring preferably has a spring receiver for supporting one end of the spring, the other end of which is abutted against the outside of the piston, a screw rod having an inside end connected to the spring receiver and having an outer screw portion, a nut member having an inner screw mating with the outer screw of the screw rod and fixed at the outside end of the cylinder, and a handle for rotating the screw rod.

According to the second aspect of the present invention, there is provided a flask with the above-mentioned material supplying device, comprising an upper half and a lower half, the plan view of each half having substantially rectangular shape, two material supplying devices arranged at two corners adjacent to the same side of one of the halves, heat-insulating members provided on a base surface and three side surfaces including the two corners of each of the halves.

When the above-mentioned supplying device is used, the means for adjusting the elastic force is adjusted to keep the force in its weakest state. Under that condition, the cavity of the flask is filled with plastic material for forming a denture base under pressure. At the same time, the cylinder is also filled with the same material under pressure. Therefore, the piston is moved outward and is stopped by the stopper.

In the above condition, even if plastic material (PMMA or thermoplastic elastomer for liner) expands under heating, the piston does not move any further since the stopper supports the piston. Therefore, the inner volume of the cavity for forming the denture base is not changed and high pressure is maintained in the cavity while the plastic material (PMMA) is heated to be polymerized or the thermoplastic material is heated to be bonded on the main body of the denture base. Therefore, neither bubbles nor mold cavities are generated in the denture base or the liner.

Further, at the appropriate time after the polymerization of PMMA begins, the adjusting means is operated to strengthen the force of the spring. In that condition, even if the plastic material (PMMA) shrinks due to progress of polymerization or cooling, the correct form is created because the same material is supplied from the cylinder.

When the liner is heated and bonded onto the main body of the denture base, the bonding is strengthened because the inner space where the denture base is formed is kept under high pressure.

Further, while cooling naturally, operating the handle member of the means for adjusting spring force to increase the spring force supplies more material to the liner to compensate even if the denture base shrinks. Therefore, bubbles and molding cavities are eliminated.

The adjusting means is operated after the polymerization begins in the above case. However, in the actual case, the means can be operated after the piston is supported by the stopper since all openings of the space are shut before the polymerization.

Hereinafter, the present invention will be explained in detail with reference to the accompanying drawings.

BRIEF DESCRIPTION OF DRAWINGS

FIG. 9 is a perspective view showing the rubber ring shown in FIG. 8;

FIG. 10 is a sectional view showing the flask of FIG. 8 at a different stage of forming;

FIG. 12 is a perspective view of an embodiment of heat-insulating members to be used with the flask of FIG. 11;

FIG. 13 is a sectional view obtained along the line XIII—XIII in FIG. 12;

DETAILED DESCRIPTION

First embodiment

Figure 1:
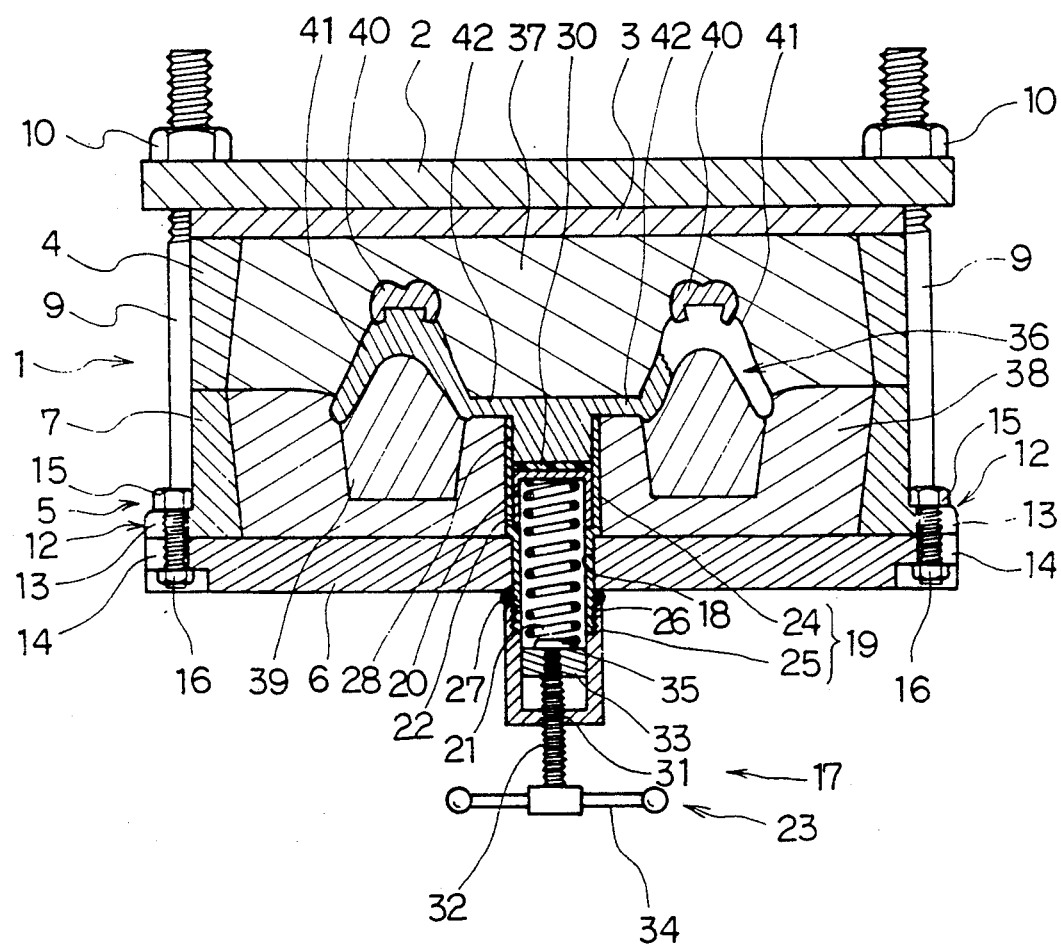
FIG. 1 is a sectional view (along line I—I in FIG. 2) showing a first embodiment of the flask of the present invention.
Figure 2:
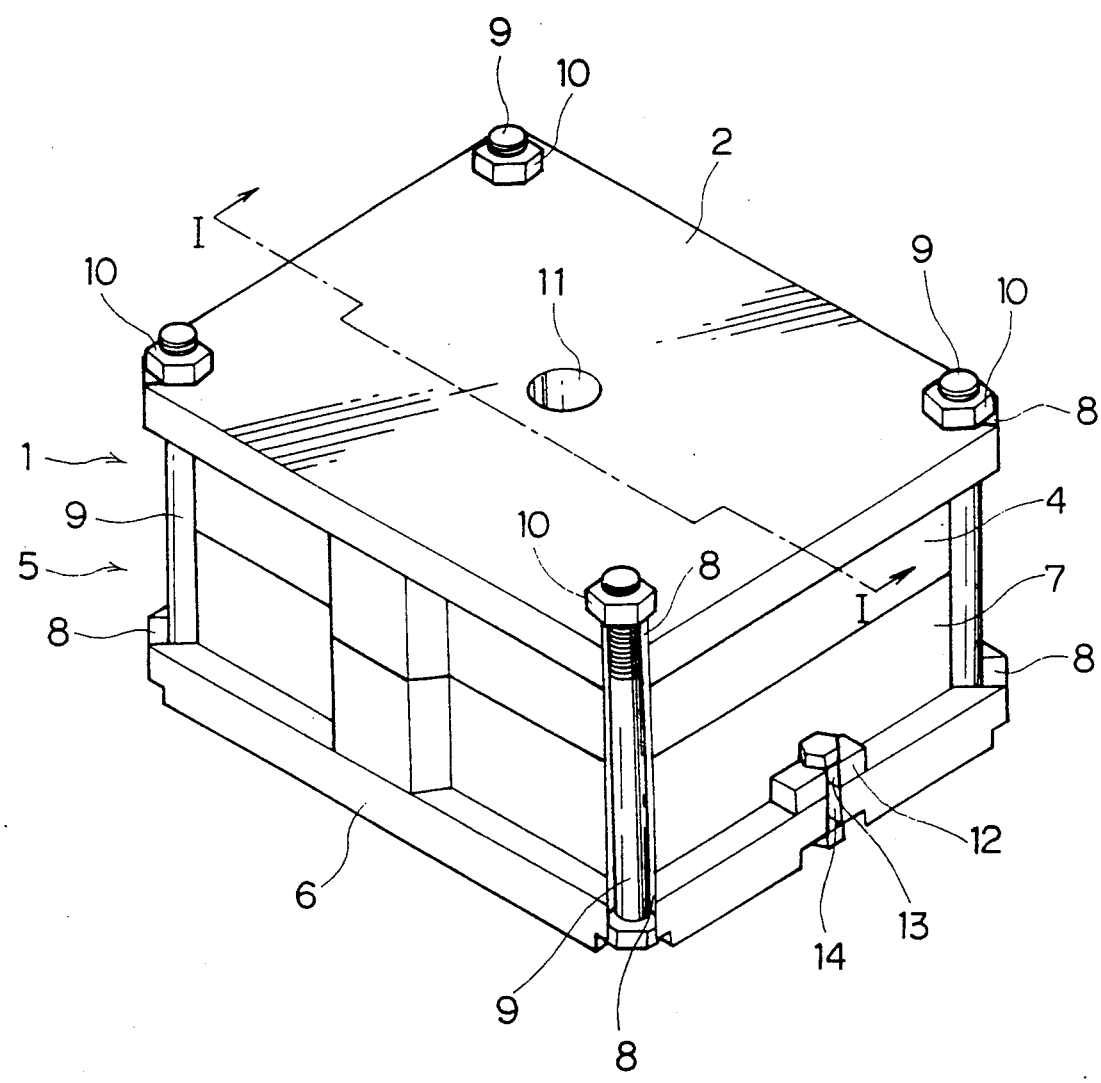
FIG. 2 is a perspective view showing the flask of FIG. 1.
Figure 3:
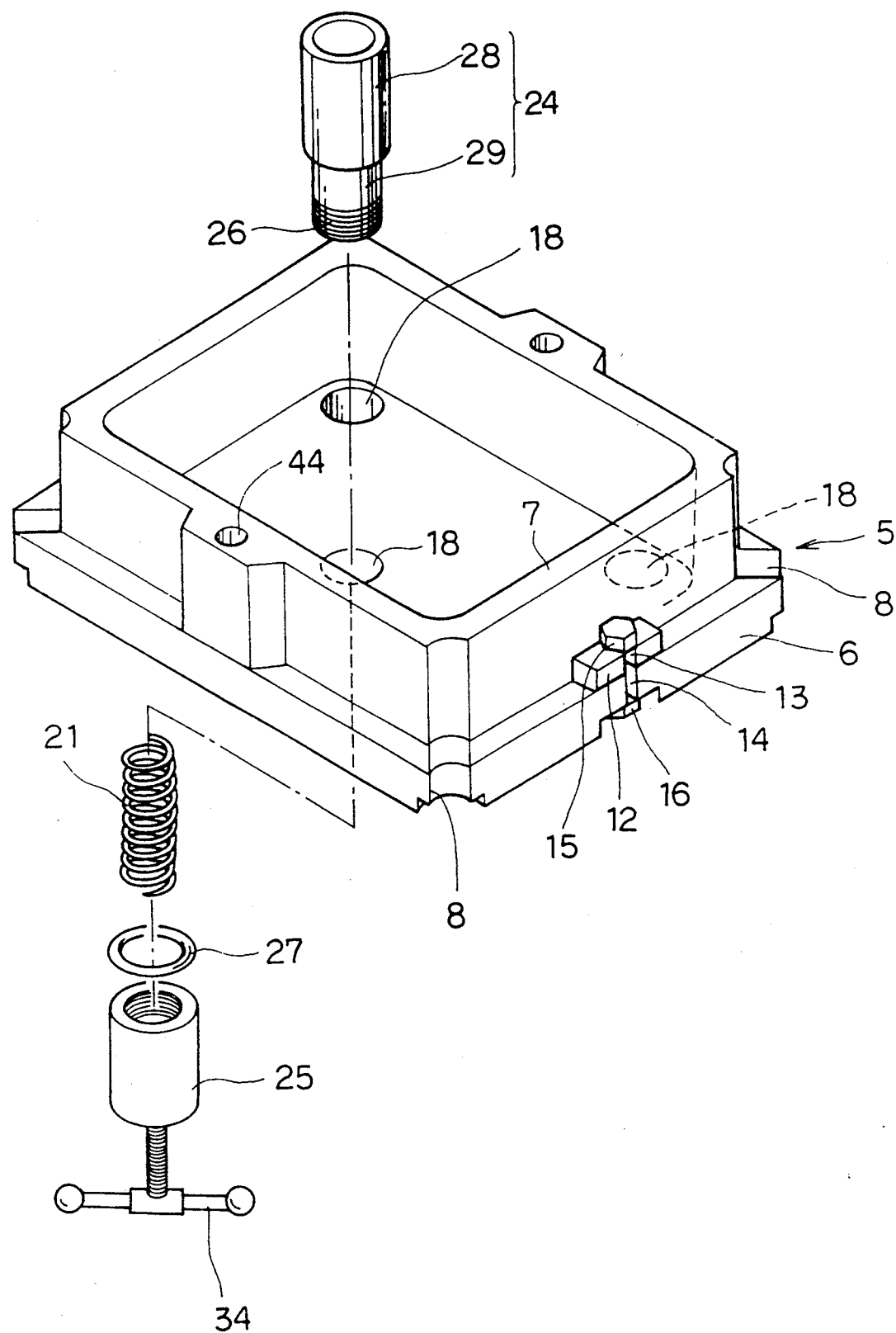
FIG. 3 is a perspective view showing the lower half of the flask shown in FIG. 2 in a state before assembling.

Referring to FIGS. 1 to 3, the numeral 1 designates an upper flask or an upper half of a flask. The upper half 1 comprises an upper lid 2, a middle lid 3 and a frame 4 which are made of metal (for example, brass, aluminum, stainless steel) and are formed to a substantially rectangular shape. The size of frame 4 is, for example, about 8 cm in width, about 10 cm in length and about 2.5 cm in height. As shown in the drawing, the inside surface of the frame slants so that the frame 4 can be easily removed from a plaster mold 37.

Numeral 5 designates a lower flask or lower half of the flask. The lower half 5 comprises a lower lid 6 and a frame 7 being rectangular in shape. Further, the inside surface of the frame slants so that the free end side is enlarged.

Upper lid 2 and lower lid 6 are slightly larger than frames 4 and 7 and middle lid 3, and they have U-shaped cut portions 8 as shown in FIG. 2.

Bolts 9 are inserted through the cut portions 8, and the bolts 9 and nuts 10 securely hold the upper lid 2 and the lower lid 6 and draw and fasten them together.

Numeral 11 of FIG. 2 designates a hole formed near the center of the upper lid 2. This hole 11 exists in middle lid 3 as well. Hole 11 is utilized for fixing the plaster 37 and for injecting material for a denture base from the outside of the flask.

Frame 7 is provided with fingers 12 projecting laterally from lower end of the frame 7. Each finger 12 has a U-shaped cut portion 13. Lower lid 6 has the same U-shaped cut portions 14. Bolts or screws 15 are inserted in the cut portions 13 and 14, and are fastened by nuts 16 to fasten frame 7 and lower lid 6.

Numeral 17 in FIG. 1 designates a material supplying device according to the present invention detachably mounted through the main side of the lower flask 5, i.e. the lower lid 6. The device 17 comprises a cylinder 19, a piston 20, a coil spring 21, a stopper 22 and a means for adjusting the elastic force of spring 21.

The cylinder 19 is inserted through hole or opening 18 formed in lower lid 6 and is attached to the lower lid 6. The piston 20 is housed in the cylinder for reciprocal linear motion. The spring 21 is housed in the cylinder, and an upper (inside) end of the spring is abutted against the lower side of the piston 20 for elastically urging the piston 20 toward the inside of the flask. The spring has a coil shape, for example, with about 10 mm in diameter and about 3.0 cm in length. The stopper 22 is a step portion formed in the cylinder 19 for restricting the stroke-end of the piston at the most descended position, i.e. the most outside position.

The inner end of cylinder 19 is open, and the outside end, situated outside of the lower flask 5, is closed. Further, the cylinder 19 is divided into a first cylinder 24 having an inside diameter of about 13 mm and a second cylinder 25 having an inside diameter of about 11 mm, such that the cylinder 19 is detachable from the flask. The second cylinder 25 is screwed onto the outer screw portion 26 of the first cylinder projecting from the outside surface of the lower lid 6. An O-ring 27 is provided between the second cylinder 25 and the lower lid 6. Further, the first cylinder 24 has an upper portion 28 (about 13 mm in inside diameter) and a lower reduced portion 29 (about 11 mm in inside diameter). The opening 18 of the lower lid 6 has a diameter slightly larger than the outside diameter of the reduced portion 29 so that the reduced portion can be inserted, and the large diameter portion 28 engages with the edge surrounding the hole 18.

The piston 20 has a cup-like shape and is provided with a seal member 30 made of rubber or the like which is fixed on the head of the cup-like member.

The first cylinder 24 has a step 22 about 1 mm in width, for example, on the inside surface at the position where the outside diameter changes, i.e. between the large diameter portion 28 and the reduced portion 29. Further, the piston 20 is made so as to slide in the large diameter portion 28. Therefore, the piston 20 is stopped by abutting against the step 22, and is prevented from descending further. The step 22 functions as the above-mentioned stopper in the present invention.

The above-mentioned spring force adjusting means 23 comprises a screw rod 32, a screw hole (nut member) 31 formed in the outside end, i.e. the closed end, of the second cylinder 25, a disc-like spring receiver 33 attached on the inside end of the screw rod 32 so as to receive the outside end of the spring 21, and a handle member 34 provided on the outside end of the screw rod 32. The spring receiver 33 is attached on the screw rod 32 by means of a bolt 35 so that rotation of the screw rod 32 is not transmitted to the spring receiver 33.

Therefore, when the handle member 34 is operated to rotate the screw rod 32, the screw rod 32 and the spring receiver 33 are moved in a direction axial to the cylinder.

The above-mentioned first embodiment of the flask of the present invention is used as mentioned hereinafter.

Referring to FIG. 1, the numeral 36 designates a hollow space for forming a denture base, and the space 36 is constructed by surrounding with solid plaster 37 and 38, and a plaster model 39 of the alveolar ridge of a patient. The space 36 can be formed by known methods using wax or the like. The numeral 40 designates artificial teeth embedded in the solid plaster 37.

The space 36 and the inner space of the first cylinder 24 are filled with plastic material for denture base, for example, PMMA dough 41. The PMMA in the space 36 and the PMMA in the cylinder 24 are connected to each other by a sprue 42 (grooves communicating from space 36 to the inner space of the first cylinder 24).

Before the space 36 and the cylinder 24 are filled with the PMMA dough 41, the spring receiver 33 of the second cylinder 25 is lowered to the outside stroke end. Then, the force of spring 21 is in its weakest state, and the piston 20 comes to rest against the step 22 of the large diameter portion 28. Therefore, the maximum volume of PMMA in the cylinder 19 is restricted. The upper lid 2 and the lower lid 6 are tightly bounded by the bolts 9 and the nuts 10. Then, the handle 34 is rotated to push the spring receiver 33 up. The spring 21 is thus compressed, and the piston is pressed forcefully against the paste-like PMMA dough 41.

The force of the spring can be adjusted by operating the handle 34. When the spring 13 is compressed to the maximum extent (i.e. to the minimum length), the pressing force is about 10 kg in this embodiment.

In the above-mentioned state, the flask is placed in a pressure cooker or the like, and is heated to about 100° to 120° C. to be polymerized.

Though the PMMA 41 expands due to heat when polymerization begins, the piston 20 of the material supplying device 17 cannot descend any further. Therefore, the interior pressure of the space 36 for forming the denture base is kept in high, and neither bubbles nor molding cavities are produced as the PMMA is polymerized, then shrinks.

Further, if the interior pressure in the space 36 falls during the polymerization and shrinkage, additional PMMA dough is supplied into the space 36 from the material supplying device 17 and deformation due to shrinking is prevented.

Since the piston 20 is stopped by abutting against the step 22, the PMMA resin 41 would not be positioned on the outside of the flask to be subjected with heat. Therefor, the temperature of the PMMA resin 41 in the cylinder rises very slowly, and the PMMA resin can be supplied into the flask for filling the shortage of material to the last.

Figure 4:
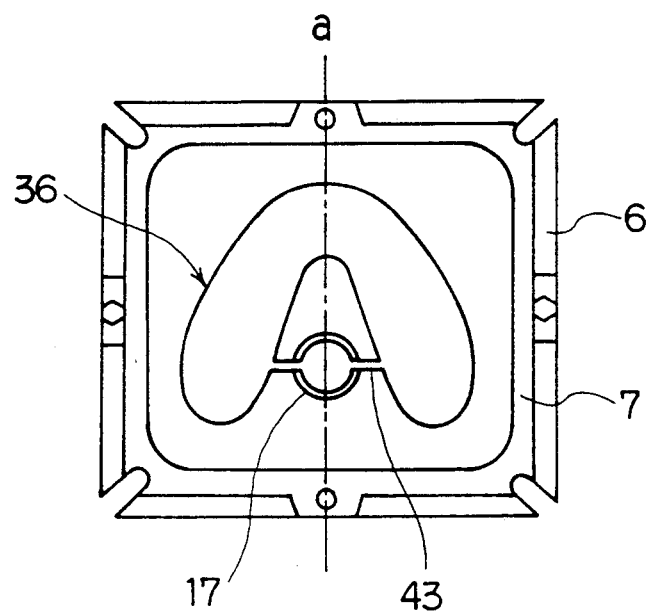
FIGS. 4 and 5 are plan views showing two embodiments of the lower half of the flask of the present invention, respectively.

FIG. 4 shows an example arrangement for the supplying device 17 when a lower denture is produced. The device 17 is positioned on a center line a and at a position shifted slightly down (to the rear). The device 17 communicates to the space 36 for forming the denture through sprue 43.

Figure 5:
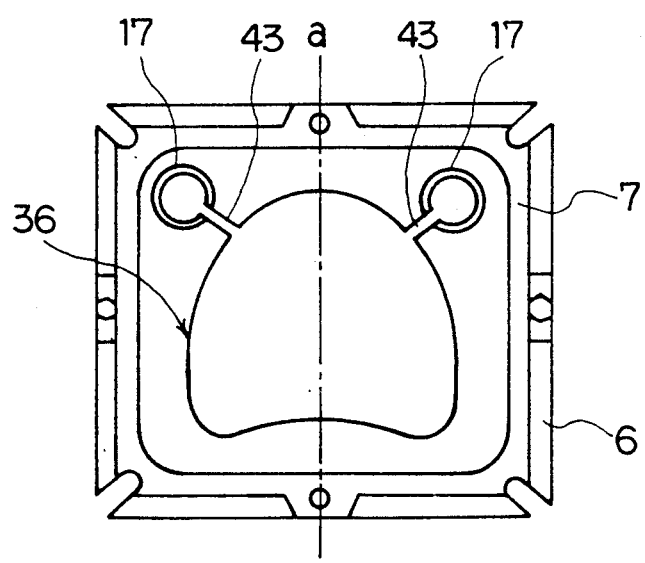

FIG. 5 shows an arrangement of the material supplying device 17 when an upper denture is produced. Two devices 17 are positioned at the upper (in the drawing) corners and communicates to the space 36 through sprues 43.

The reason why the frame 7 of the flask has a rectangular shape is to obtain spaces for positioning the supplying devices 17. The numeral 44 designates small openings formed in the frame 7 for positioning the frames 1 and 7. Pins (not shown) or the like provided on the upper frame 1 at the corresponding positions are inserted through the opening 44 of the frames 7 in order to correctly put the upper frame 1 on the lower frame 7.

Second embodiment

In FIGS. 6 through 10, there are shown the second embodiment of the flask of the present invention where a liner made of thermoplastic elastomer to be formed and bonded on the back surface (mucous membrain surface) of a denture base is used.

Figure 6:
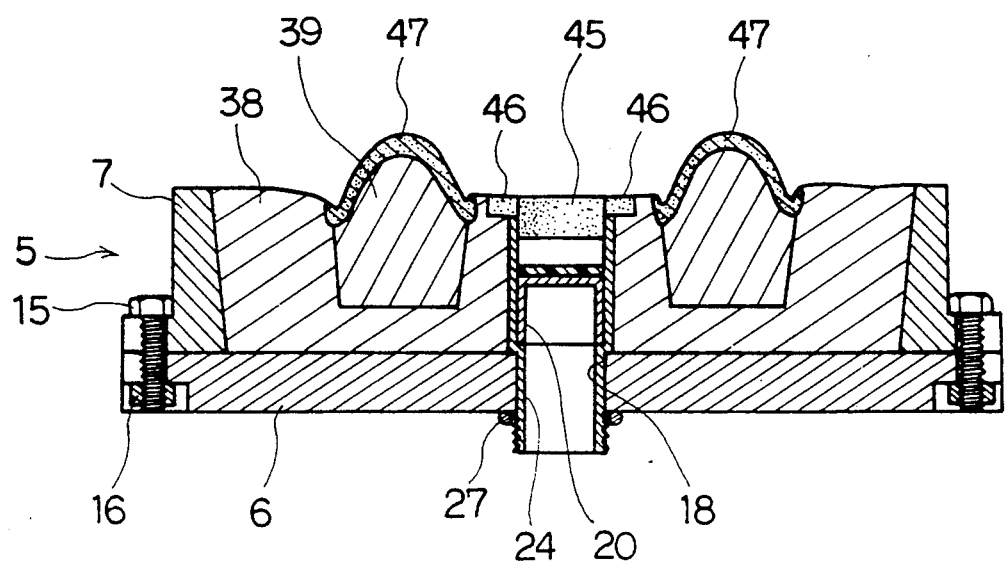
FIG. 6 is a sectional view showing the lower half of a second embodiment of the flask of the present invention.

Referring to FIG. 6, the numeral 5 designates a flask, and the numerals 6 and 7 designate a lower lid and a lower frame, respectively. The lower lid 6 and the lower frame 7 are fixed to each other by bolts 17 and nuts 16 as described above with reference to FIG. 1.

The numeral 39 designates a plaster model embedded in solid plaster 38, and the numeral 24 designates the first cylinder of a material supplying device 17. The cylinder 24 is inserted into a hole 18 and temporarily fixed to the lower lid 6 before the plaster 38 is poured in the flask 5. A piston 20 is slidably inserted the first cylinder 24.

Figure 7:
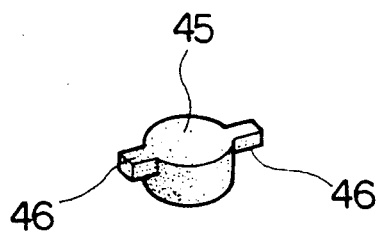
FIG. 7 is a perspective view showing the rubber plug shown in FIG. 6.

The open inside end of the first cylinder is plugged with a rubber plug 45 in order to prevent the plaster 38 from entering the first cylinder 24. As shown in FIG. 7, the rubber plug 45 has two lateral projections 46 for forming sprue grooves.

A wax layer 47 is placed on the plaster model 39 and is formed to a shape corresponding to the liner to be formed.

After the wax layer 47 is formed, the frame 4 of the upper flask 1 is put on the lower flask 5, liquid plaster 52 (see FIG. 8) is poured into the frame 4, and a middle lid 3 is put thereon.

After the plaster 52 sets, the flask is dipped in hot water of 100° C. Then, the wax layer 47 is softened. After the upper and lower halves of the flask are separated, the lower half is further heated by dipping in hot water to completely remove the wax. The above-mentioned middle lid 3 and the frame 4 are utilized as a pressing die for forming the liner.

Figure 8:
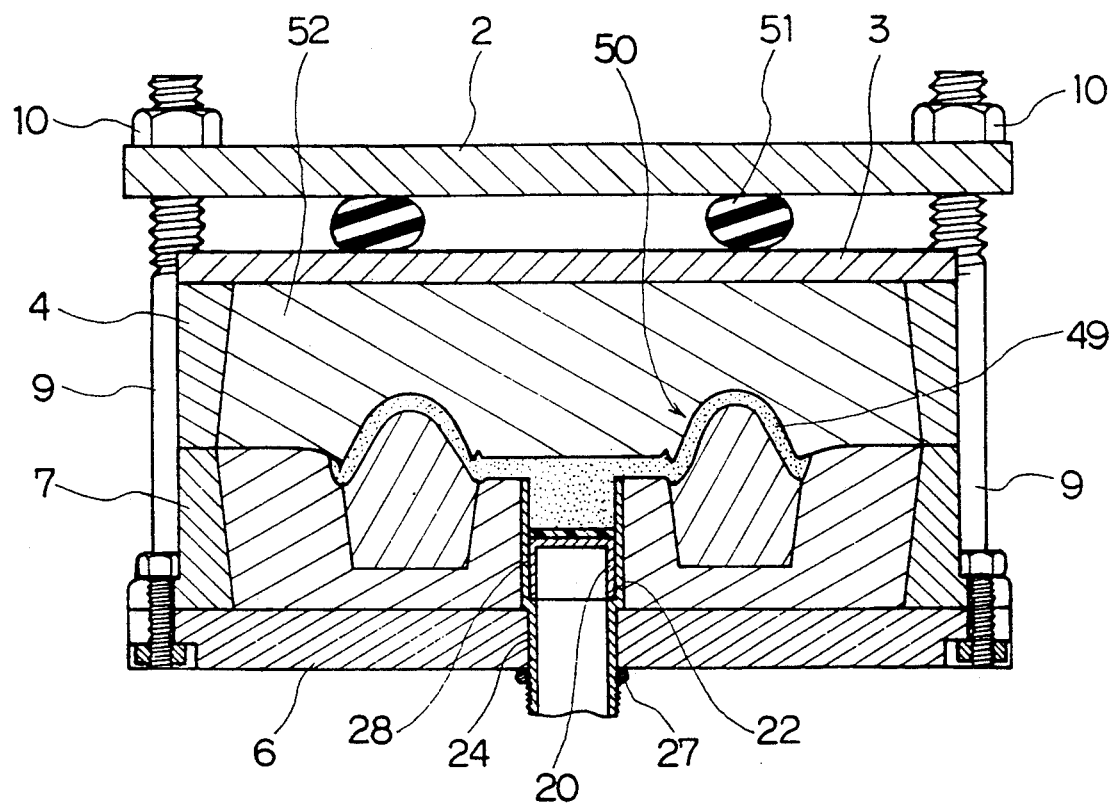
FIG. 8 is a sectional view showing the second embodiment of the flask of the present invention.

In the next step, the rubber plug 45 is removed as shown in FIG. 8, and a previously heated and softened material 49 made of thermoplastic elastomer for the liner is inserted between the pressing die and the lower flask 5. Therefore, the space for forming the denture base, i.e. a space 50 for forming a liner in the present case, and the space in the large diameter portion 28 of the first cylinder 24 are filled with the material of liner 49. With the present construction, the piston 20 is stopped by abutting against the step 22. Olefin thermoplastic elastomer is the preferred, but not necessarily only, lining material.

At the next step, in the present embodiment, a rubber ring 51 is sandwiched between the middle lid 3 and the upper lid 2, and the upper lid 2 and the lower lid 6 are fastened to each other by bolts 9 and nuts 10. At this point, the rubber ring 51 is compressed due to the clamping of the bolts 9 and nuts 10, and it applies constant and regular elastic pressure between the pressing die and the lower flask 5.

In this state, the flask 5 is dipped in hot water (about 100° C.). The excess liner, heated and softened in hot water, flows out as mold flashing, and more accurately shaped lining is obtained.

FIG. 9 shows an embodiment of shape of the rubber ring 51. The rubber ring 51 can be formed of silicone rubber, or the like.

After the liner 49 is formed as described above and the first cylinder 24 is filled with additional material for liner 49, the pressing die is removed. Then, the outside surface of the liner 49 is coated with a bonding or adhesive agent. Then, as shown in FIG. 10, instead of the pressing die, the upper flask 1 having a space 36 for forming the denture base including a space for forming the lining is put on the lower flask 5 so as to clamp the PMMA dough 41 therebetween.

At this step, the upper flask 1 is trial-pressed against the lower flask 5 several times, and the PMMA flashing is cut and removed.

The plaster 37 in the upper flask 1 is previously prepared by building wax onto the plaster model 39, forming the wax to the shape of the denture base to be formed, arranging artificial teeth 40 to make a denture model, and then removing the wax. Known methods can be used to embed and fix the artificial teeth in the plaster 37.

Then, the upper lid 2 is put on the middle lid 3, and the upper lid 2 and the lower lid 6 are fastened by means of the bolts 9 and the nuts 10. Next, the handle 34 is operated to compress the spring by about one half to one third of full compression. This step is performed to prevent bubbles, mold cavities, and the like from forming in the PMMA when the PMMA 41 is polymerized and set as in the above mentioned first embodiment.

Thereafter, the flasks 1 and 5 are dipped in a pressure cooker, and are heated to about 100° to 120° C. Then, the PMMA 41 is polymerized and set, and the liner 49 is bonded to the PMMA at the same time.

After the flasks 1 and 5 are heated for about five minutes, the flasks 1 and 5 are taken out of the pressure cooker. The handle 34 is operated then immediately to compress the spring to the maximum compressed state, and pressure is thereby applied to the lining material 49 in the first cylinder 24 through the piston 20. Thereafter, the flasks 1 and 5 are naturally cooled.

However, in an actual work, the handle 34 can be operated (i.e. the spring can be compressed) before the flasks 1 and 5 are heated. Such method may be easy to perform.

During the natural cooling, the liner 49 shrinks. However, since additional lining material is supplied from the first cylinder 24, the liner remains free of bubbles, mold cavities and deformation.

Since the piston 20 is stopped by abutting against the stopper step portion 22, the liner 49 would not be positioned on the outside of the flask to be subjected with heat. Therefore, the temperature of the liner rises very slowly, and the liner 49 can be supplied to the last.

As an experiment, a coil spring of 0.7 kg/mm in spring constant and 30 mm in normal length is used. The coil spring can effect 10 kg pressing force when compressed by 15 mm.

Under the above-mentioned condition, the amount of lining material on the back surface of the denture base is about 6 grams, and the amount of material additionally supplied from the supplying device 17 is about 1 gram.

Though two procedures for forming the denture base (including liner) are described above, the device and flask of the present invention is not limited to them. It can be utilized for forming orthodontic tools, mouthpieces, attachments, jaw restoration material, or the like. In this specification, the word "denture base" includes the above-mentioned tools.

Third embodiment

The conventional flask is generally formed in a shape corresponding to the shape of a denture, i.e. in a semicircle shape. However, when such flasks are used and dipped in hot water to set the denture base embedded in the plaster by heat polymerization, heat is conducted from the peripheral surfaces to the center and the denture is gradually set from the peripheral portions thereof.

Generally, the peripheral portions, i.e. alveolar portion, cheek side portions and lip side portions are thick, and the center semicircular portion, i.e. palate portion is thin. Therefore, the palate portion which is heated later is strongly influenced by shrinkage due to the polymerization.

That is to say, the material of the palate portion, which set firstly, is pulled in the direction of shrinkage during the polymerization of the peripheral thick portions, and is noticeably deformed. In fact, in the denture prepared by conventional methods, there is usually a gap between the palate portion of an upper denture and mucous membrane of the patient's palate. Therefore, the denture cannot be in close contact the mucous membrane.

Further, when deformation takes place in the interior of the denture base, the denture deforms further when taken out of the plaster due to the interior strain or deformation. Thus, artificial teeth of the upper and lower dentures cannot correspond to each other precisely.

The third embodiment of the present invention has been improved in order to keep the deformation to a minimum. The third embodiment is described hereinafter in detail with reference to FIGS. 11 to 17.

Figure 11:
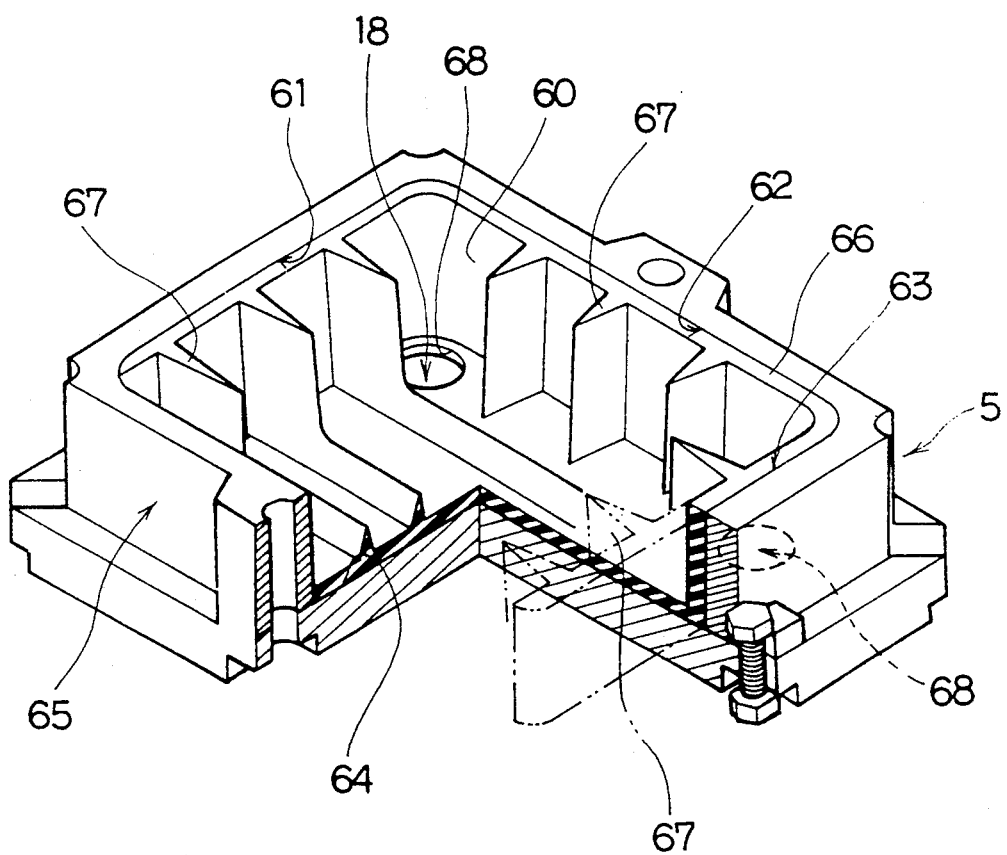
FIG. 11 is a partially cut away perspective view showing a lower half of the third embodiment of the flask of the present invention.

Referring to FIGS. 11 and 13, the numeral 5 designates a lower flask as in the above-mentioned embodiments. Numeral 60 designates a heat-insulating member made of a material having good heat-insulation, such as silicone rubber, which is contained in the flask 5. The heat-insulating member 60 is formed to cover three inside walls 61, 62, 63 including the corners where holes 18 are formed, and a bottom surface 64 which is a main inside surface.

The remaining side surface 65 of the flask 5 is free from heat insulation.

Figure 14:
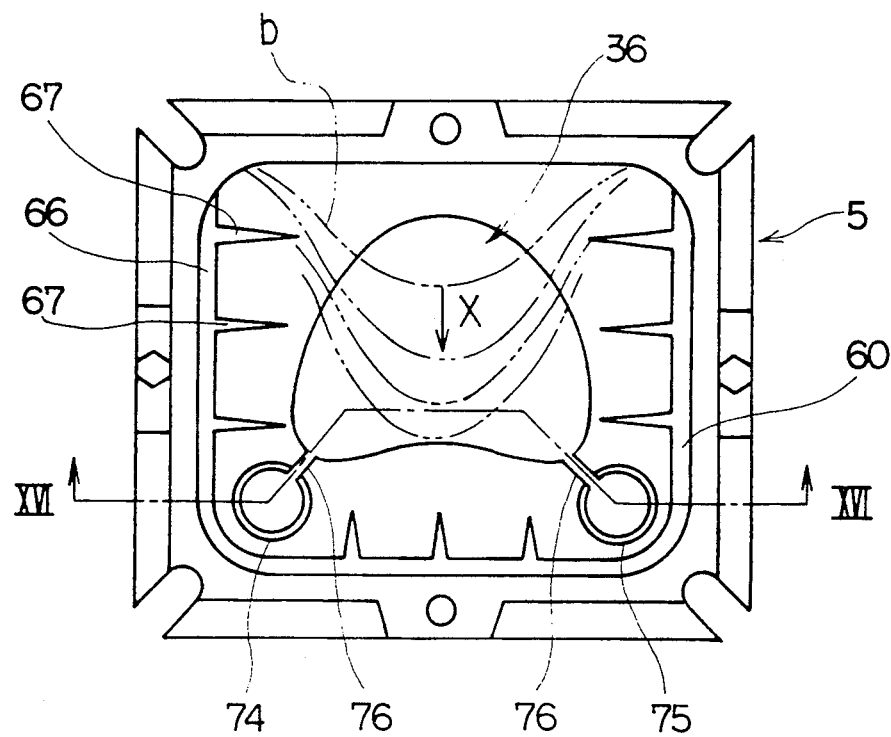
FIGS. 14 and 15 are plan views showing embodiments of the lower half of the flask when used.
Figure 15:
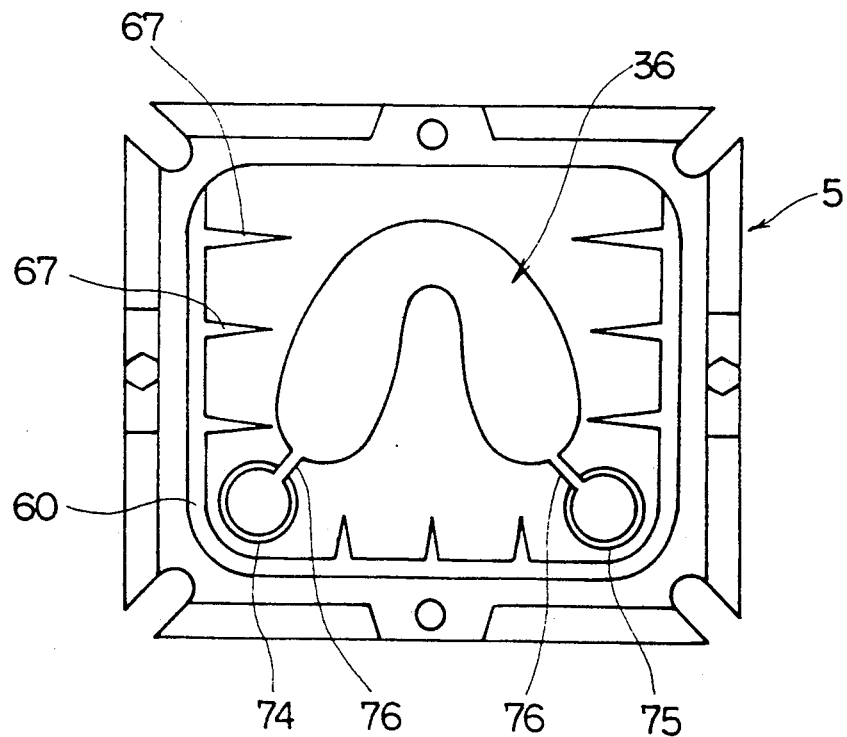

As mentioned below, heat is applied through the insulation-free side, and is gradually conducted toward the corners surrounding the holes 18 as shown in FIG. 14 by lines b and arrow X.

The heat-insulating member 60 comprises laminer portions 66 of about 3 to 6 mm in thickness covering the above-mentioned three side surfaces and the bottom surface, and plural fins projecting from the laminer portions 66 toward the interior of the flask 5.

The length of the fins 67 should be such that the free end of each fin reaches the denture model leaving only a slight gap or is actually in contact with the denture model. Even if the fin is in contact with the denture model, there is no problem since the fin is flexible.

Fins 57 near the insulation-free side, i.e. fins situated at mesial are larger than the other fins. The fins are provided to ensure that heat is conducted from only the insulation-free side. That is to say, the temperature will be lowest at the holes 18 due to the placement of the fins. Further, since the fins separate plaster, the solid plaster can be easily broken when the denture is taken out of the plaster. Numeral 68 designates a hole of the same size as the holes 18 of the flask 5. They are positioned to align with those holes 18.

The same heat-insulating member 69 is also provided in the upper flask 1 (see FIG. 12). The heat-insulating member 69 has a lid member 71 made of the same material at the upper side 70, and liquid plaster can be poured into the flask 1 through the opening after the lid member 71 is removed. There is a formed step between the lid member 71 and the upper surface of the heat-insulating member, and therefore, the lid member 71 is prevented from falling into the upper flask 1. Further, the under surface of the lid member 71 is also provided with heat-insulating fins 73.

As shown in FIG. 13, the center of the lid member 71 is thick, and the fins 73 are provided on the under surface of the thick portion. The thick portion corresponds to the palate portion of the denture, and a large heat insulating effect is obtained there.

FIG. 14 shows the arrangement of a space 36 for forming a denture base and the first and second supplying devices 74,75 in the lower flask 5. In this arrangement, the first and the second supplying devices 74,75 are positioned near the peripheral portions.

In the drawing, the numeral 76 designates sprues communicating to the peripheral portion of the space 36 for forming denture base from the supplying devices 74 and 75.

Figure 16:
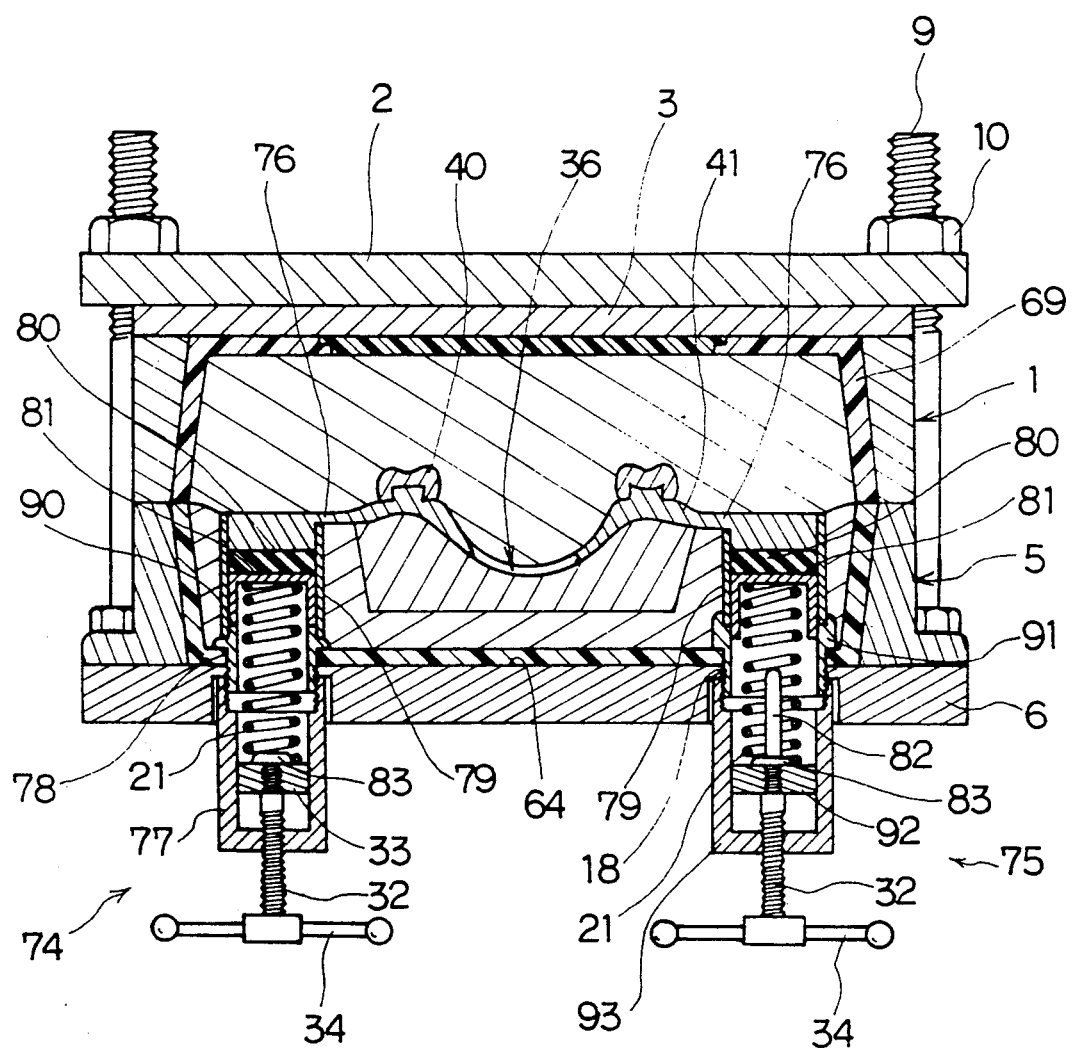
FIG. 16 is a sectional view obtained along the line XVI—XVI of FIG. 14.

FIG. 16 is a sectional view showing the lower flask 5 shown in FIG. 14, on which an upper flask 1 with embedded artificial teeth 40 has been placed.

The first supplying device 74 is attached to one of the holes 18 (to left of drawing), and the second supplying device 75 is attached to the other hole 18 (to right of drawing).

Each of first and second supplying devices 74 and 75 has an inside cylinder 78 and a cylinder pipe 79. The cylinder pipe 79 is made of low-heat-conductive material, such as fluorine-containing resin, and the inside cylinder is made of metal.

The structure of the first supplying device is such that the cylinder pipe 79 fits on the outside of the inside cylinder 78, and a piston 81 is stopped by abutting against an end 90 of the inside cylinder 78. That is to say, the end 90 functions as a stopper. The numeral 77 designates the second cylinder situated outside the flask. On the other hand, the second supplying device 75 is constructed such that the cylinder pipe 79 is inserted inside the inside cylinder 91. The cylinder pipe 79 and the inside cylinder have the same inside diameter in order to allow the seal member and the piston to slide through the cylinder pipe 79 and the inside cylinder 91.

A pin 81 is fixed to an upper portion as a stopper for restricting the descent of the piston 81. The numeral 92 designates a spring receiver, and the numeral 93 designates a second cylinder. The remaining parts are the same as the first supplying device 71.

It is necessary to match the inside diameters of the cylinder pipes 79 to the first and the second supplying devices 74 and 75. Further, the springs 21 of the devices having the same spring force are used. The uformity in the designs of the devices is to provide the same material-supplying capacity to each device. The spring force of the spring 21 is preferably about 2 to 5 kg/cm$^2$.

The above-mentioned devices can be operated as same as the first embodiment.

That is, the handle 34 is rotated with fingers to press up the spring receivers 32 and 92. When the springs 21 are compressed, the combined flasks are dipped in hot water to polymerize the material.

During the polymerization, the flasks are put in a pressure cooker (not shown) such that the insulation-free side is directed to the lower side, and level of hot water is adjusted to reach the center of the denture. In this situation, heat is conducted from the center portion to the peripheral portion of the denture, and the peripheral portion is polymerized and set last.

Therefore, material is continuously supplied from the first and second supplying devices 74 and 75 till the final stage, and a denture free of deformation is produced.

Figure 17:
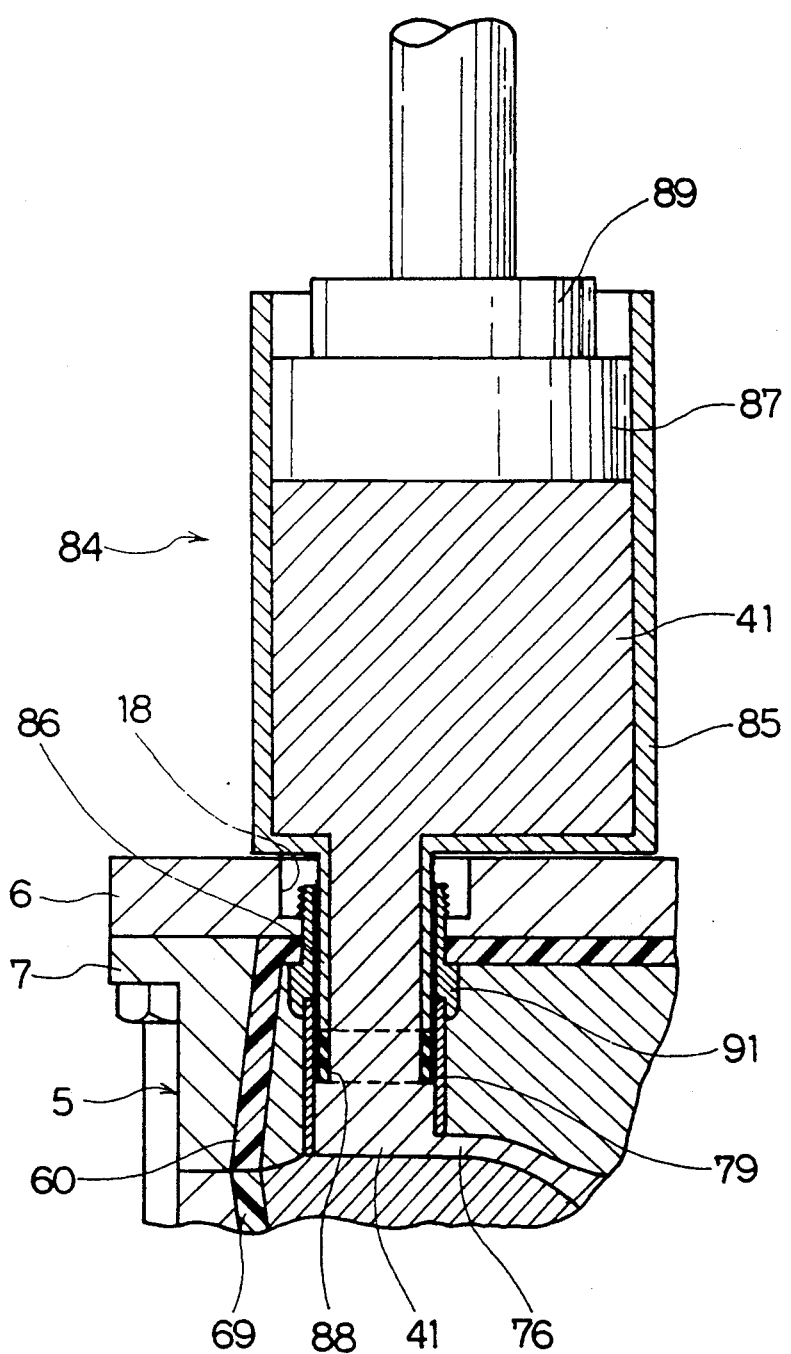
FIG. 17 is a sectional view in part showing an embodiment of the charging device used in the present invention.

FIG. 17 shows a material charging device 84 to be used at the step before the step shown in FIG. 16. That is, the device is used when a space 36 for forming a denture base is charged with denture material. In this step, the charging device 84 is attached in place of the second cylinder 93 of the second supplying device. The charging device comprises a cylinder 85, a charging tube 86 and a piston 87, which are made of metals or plastics. The numeral 88 denotes an elastic tube made of elastomeric material such as rubber. The elastic tube 88 is expanded in diameter due to injection pressure when material is charged, and because the tube fits against the cylinder pipe, it provides a sealing effect.

The cylinder 85 is made with a volume capable of containing material for forming a denture two or three times. Numeral 89 designates the piston of a hydraulic pressing machine.

Hereinafter, the function and operation of the charging device 84 will be explained.

At first, the cylinder 85 is filled with PMMA dough with an amount sufficient for at least one denture, and the injection tube 86 is inserted into the opening 18.

Then, the device is put on a hydraulic pressing machine together with the flask. The piston member 87 is pressed with the piston 89 to inject the PMMA 41 to the space 36 for forming the denture base through the cylinder pipe 79 and the sprues 76. At this time, the second cylinder 77 of the first supplying device 74 (see FIG. 16) is removed.

After the space 36 for forming the denture base is filled with the resin 41, the resin 41 flows into the cylinder pipe 79 of the first supplying device 74 through the sprue 76, and the cylinder pipe 79 is filled. By pushing the piston from the outside, the operator can know whether the pipe 79 is completely filled with resin or not.

After the operator confirms the fact that the piston 81 is abutted against the stopper and has stopped, injection of resin is also stopped. Then, a spring 21 is inserted into the inner cylinder 81 of the first supplying device 74, and the second cylinder 77 is attached.

Next, the injecting device 84 is removed from the flask, the sealing member 80 and the piston 81 are inserted into the inner cylinder 91, the spring 21 is housed, and the second cylinder 93 is set in place.

Thus, the first and second supplying devices 74 and 75 are attached to the flask, and by rotating the handles 34 to compress the springs 21, the resin 41 can be automatically supplied into the space 36 for forming a denture base.

Though, in the above embodiment, a hydraulic stamping machine is used as the driving force for pressing the piston of the charging device 84, compressed air can also be utilized for that purpose.

Using the present invention, the material for a denture base is supplied from a supplying device, as the denture base is polymerized or the liner included in the denture base is heated. Therefore, even if the denture base shrinks when the denture base is heated for polymerization or cooled after the polymerization, the interior pressure of the flask is kept high, and bubbles and mold cavities are prevented.

Especially, when the material of the denture base is PMMA, conventional devices present the problem of polymerization shrinkage. However, using the supplying device of the present invention, a denture base having a back mucous membrane surface precisely corresponding to the alveolar ridge of patient can be obtained, and the setting will feel good.

If the denture base material is for a liner, the liner tends to shrink and the interior pressure of the flask is reduced when the liner is cooled after heating. In addition, a shortage of material results along with bubbles and molding cavities.

However, by using the supplying device of the present invention the bubbles and molding cavities can be prevented since the material of the liner is charged with pressure by the supplying device. Further, a liner with the outer surface precisely corresponding to the mucous membrane surface can be obtained.

Further, in the supplying device of the present invention, material for a denture base or a liner can be charged after the spring is loosened (or at appropriate time) since the device has a spring force adjusting means. Therefore, the material can be easily charged, and the device can be easily operated.

When the denture base material is heated for setting, the interior pressure can be controlled for medium or maximum pressure by operating the handle. Therefore, when the denture base is polymerized or when the liner is cooled, the most suitable pressure can be applied in accordance with the situation.

Further, in the present invention, the size of spring contained therein is not limited since the device is installed on the main side of the flask such that it projects outside of the flask. Therefore, a very strong spring can be employed and sufficient pressure can be applied for any denture base to be formed.

Further, in the flask of the present invention, by providing heat-insulating members on the inside surfaces of the flask excepting one side surface and by providing the supplying device at the first position to which the heat is conducted, strain and deformation during polymerization of the denture base material can be effectively prevented, and a denture precisely corresponding to the alveolar ridge can be obtained.

Though several embodiments of the present invention are described above, it is to be understood that the present invention is not limited to the above-mentioned embodiments, and various changes and modifications may be made in the invention without departing from the spirit and scope thereof.

What we claim is:

1. A device for supplementing supply of plastic material into a dental flask under pressure, comprising:
   a cylinder having a first, open-ended portion made of a low-heat-conducting material having an inner surface and extending into said flask and in communication with a denture-forming cavity therein, and a second, closed-end portion outside said flask;
   a piston slidably inserted in and housed within said first cylinder portion;
   a spring means mounted inside the cylinder for urging said piston inwardly of said flask;
   a stopper means extending radially inwardly of said first cylinder portion from said inner surface thereof and at an inner flask surface for restricting movement of said piston outwardly of the flask and to a position within said first cylinder portion, thereby forming within said first cylinder position inside said flask a reservoir for supply of a flowable polymerizable material to said denture-forming cavity within the flask while plastic material in said denture-flowing cavity is polymerizing;
   a threadedly rotatable adjusting means bearing on an outer end of said spring means and extending through a cooperatively threaded opening in the closed end of said second cylinder portion for adjusting elastic force of said spring means and thereby pressure exerted by said piston on plastic material within said reservoir and said denture-forming cavity, and wherein, at the outermost position of said piston in contact with said stopper means, said spring means is in its most extended and weakest state whereby the volume of the first cylinder portion available as a reservoir for plastic has a fixed maximum value.

2. The device of claim 1, wherein said adjusting means comprises a spring receiving portion abutting against an outside end portion of said spring, a screw-mechanism for moving said spring receiving portion in an axial direction of said cylinder; and a handle member means for operating said screw-mechanism.

3. The device of claim 2, wherein said screw mechanism comprises a nut element fixed on one outside end portion of said cylinder and a screw rod having an outer thread portion engaged with an inner thread portion of said nut element; and wherein said handle member means is fixed on one outside end portion of said screw rod.

4. The device of claim 1, wherein said cavity of said flask has a form corresponding to a denture base.

5. The device of claim 1, wherein said flask includes an inner surface which has a form corresponding to a liner of a denture base formed within said flask.

6. The device of claim 1, further comprising:
   at least two material supplying devices arranged at two corners adjacent to each other in one of upper and lower portions of said flask; and
   at least one heat-insulating member fixed on bottom and inside surfaces of three side walls surrounding said two corners of each of said upper and lower portions.

7. The flask of claim 6, wherein said heat-insulating member comprises laminar portions covering said inside surfaces of each of said upper and lower portions and fin portions projecting inward from said laminar portions.

* * * * *